United States Patent [19]

Twardowski et al.

[11] Patent Number: 5,171,227
[45] Date of Patent: Dec. 15, 1992

[54] SEPARABLE PERITONEAL DIALYSIS CATHETER

[75] Inventors: Zbylut J. Twardowski; Ramesh Khanna; W. Kirt Nichols; Karl D. Nolph, all of Columbia, Mo.

[73] Assignee: The Curators of the University of Missouri, Columbia, Mo.

[21] Appl. No.: 686,186

[22] Filed: Apr. 16, 1991

[51] Int. Cl.$^5$ .................. A61M 5/32; A61M 25/00
[52] U.S. Cl. ........................... 604/175; 604/283
[58] Field of Search ............. 604/29, 280, 283, 264, 604/905, 175

[56] References Cited

U.S. PATENT DOCUMENTS

| | | | |
|---|---|---|---|
| 4,346,703 | 8/1982 | Dennehey et al. | 604/29 |
| 4,392,855 | 7/1983 | Oreopoulos . | |
| 4,431,426 | 2/1984 | Groshong et al. | 604/280 |
| 4,592,749 | 6/1986 | Ebling et al. | 604/283 |
| 4,668,217 | 5/1987 | Isono | 604/49 |
| 4,687,471 | 8/1987 | Twardowski et al. | 604/175 |
| 4,772,269 | 9/1988 | Twardowski et al. | 604/175 |
| 4,790,810 | 12/1988 | Pugh, Jr. et al. | 604/8 |
| 4,935,004 | 6/1990 | Cruz . | |
| 4,963,129 | 10/1990 | Rusch | 604/8 |
| 5,057,075 | 10/1991 | Moncrief et al. | 604/49 |
| 5,074,846 | 12/1991 | Clegg et al. | 6704/164 |

OTHER PUBLICATIONS

Twardowski and Dobbie et al. Morphology of Peritoneal Dialysis Catheter Tunnel, Peritoneal Dialysis International, vol. 11 (1991) pp. 237-251.
Artical by Twardowski and Prowant et al. ASAIO Transactions, 1990, vol. 36, No. 3, pp. M491-M494.
Tenckhoff and Schechter, Amer. Soc. Artif. Int. Organs, 1968, vol. XIV Trans., pp. 181-187.
Article by Twardowski and Prowant entitled Can New Catheter Design Eliminate Exit-Site and Tunnel Infections? Perspectives in Peritoneal Dialysis, 1986 for (2): pp. 5-9.
Abstract of Twardowski and Prowant et al. Culture Results of Peritoneal Catheter Peri-Exit Smears (S) and Sinus Tract Washouts (W), XIth International Congress of Nephrology, Tokyo, Jul. 15-20, 1990 p. 259A.
Twardowski and Prowant et al. Key Factors in Exit Site (S) (ES) Evaluation, XIth International Congress of Nephrology, Abstracts, Tokyo, Jul. 15-20, 1990, p. 26A.
Twardowski and Nolph et al., Peritoneal Dialysis Bulletin, Oct.-Dec., 1985, pp. 219-223.

Primary Examiner—John D. Yasko
Assistant Examiner—Adam J. Cermak
Attorney, Agent, or Firm—Gerstman & Ellis, Ltd.

[57] ABSTRACT

A peritoneal dialysis catheter comprises a distal tubular section and a proximal tubular section, connected together by a nonintegral tubular connector so that the respective sections are connected together in sealed flow relation. Such a catheter may be surgically implanted in the peritoneal cavity, extending to the chest of the patient with an end thereof protruding from the chest. The respective ends of the catheter section may be connected to each other through the tubular connector as the tubular sections are surgically implanted, and typically after such implantation is substantially complete.

12 Claims, 2 Drawing Sheets

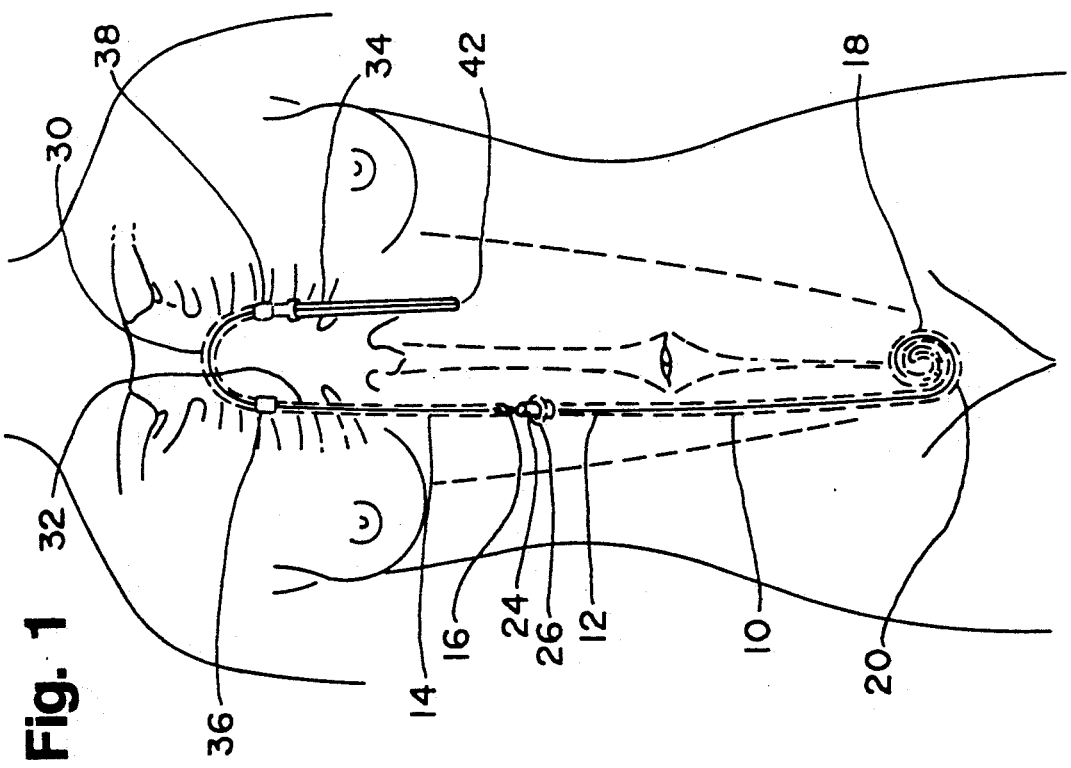
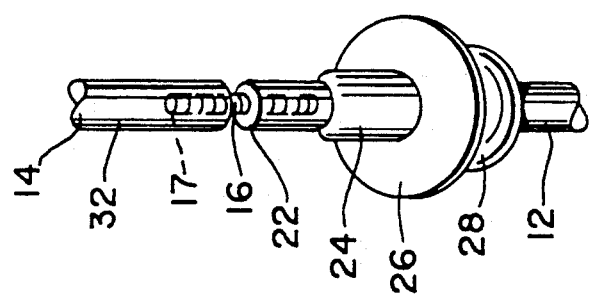
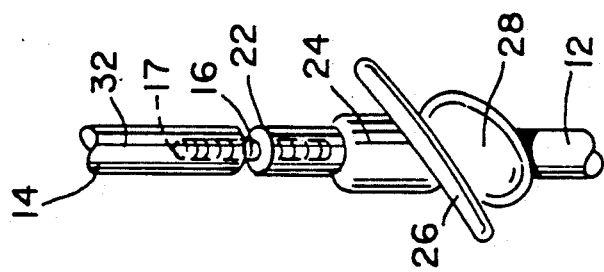

SEPARABLE PERITONEAL DIALYSIS CATHETER

BACKGROUND OF THE INVENTION

Percutaneous access to the peritoneal cavity is necessary for uremic patients who must undergo peritoneal dialysis for treatment of acute or chronic renal failure. Such an access permits infusion of dialysis solution into the peritoneal cavity and drainage of dialysate-containing wastes that are convected or diffuse from uremic blood.

Typically a peritoneal catheter is implanted through the abdominal wall. Catheter implantation creates three segments: the intraperitoneal catheter segment is the part of the catheter located intraperitoneally; the intramural catheter segment is the part of the catheter contained within the abdominal wall; and the external catheter segment is the part of the catheter outside the skin exit.

The peritoneal catheter typically comprises a catheter body or tubing plus the cuffs. The tubing is typically made of soft material such as silicone rubber or polyurethane. A cuff is a band of fabric, affixed to the intramural segment of the catheter body, for fibrous tissue ingrowth to stabilize the catheter and to prevent pericatheter bacterial penetration.

A peritoneal catheter tunnel is surgically created during the implantation. The tunnel is a passageway through the abdominal wall within which the intramural segment of the peritoneal catheter is contained. The tunnel has an internal and external exit. The internal tunnel exit, or intraperitoneal tunnel entrance, is the inlet of the tunnel into the peritoneal cavity. The skin exit is the external exit or skin outlet of the tunnel.

The cuff located close to the endoabdominal fascia is called the epiperitoneal cuff, inner cuff, internal cuff, or deep cuff. The cuff located closer to the skin is called the subcutaneous cuff, outer cuff, superficial cuff, or external cuff. A part of the tunnel between the skin exit and the outer cuff is called the sinus tract. The exit site is the most external part of the sinus tract and the skin surrounding the skin exit.

Four major complications of the implantation and use of peritoneal dialysis catheters include external cuff extrusion, obstruction (which is usually, a sequel of catheter tip migration out of the true pelvis with subsequent omental wrapping), skin exit or tunnel (exit/tunnel) infection, and dialysate leaks. Peritonitis, particularly a refractory one, may also be related to peritoneal catheter design and care. These complications result in technical difficulties, morbidity, prolonged antibiotic therapy, catheter failure, and sometimes the inability to continue peritoneal dialysis. According to The National CAPD Registry Special Survey, in 1987, overall survival of the most commonly used catheters ranged between 10-30 percent at 3 years.

The prior art disclosed in U.S. Pat. Nos. 4,687,471 and 4,772,269 (Twardowski et al '471 and Twardowski et al '269) addressed these problems and solved them partially by use of "swan neck" catheters: 1) exit/tunnel infection by a downwardly directed skin exit, 2) pericatheter leaks by placement of the deep cuff in the rectus muscle, 3) catheter tip migration by caudal direction of the intraperitoneal segment, and 4) outer cuff extrusion by a permanent bend between the cuffs. U.S. Pat. No. 4,935,004 (Cruz '004) utilized similar principles as applied in Twardowski '269 to reduce complications. Results achieved with Cruz '004 are not published yet.

Recently published results obtained with swan neck catheters in four Central Missouri hospitals confirmed theoretical expectations. An overall survival of 64% at 36 months for swan neck catheters was significantly better than that of 29% for "standard" catheters (Twardowski Z.J., Prowant B.F., Khanna R., Nichols W.K., Nolph K.D.: Long term experience with Swan Neck Missouri catheters. ASAIO Transactions 1990; 36: M491-M494.). "Standard" catheters were Tenckhoff (Tenckhoff H., Schechter H.: A bacteriologically safe peritoneal access device. Trans Am Soc Artif Intern Organs 1968; 14: 181-187.14: 181-187) and the Toronto Western Hospital catheter (U.S. Pat. No. 4,392,855).

In spite of this progress the results are still not totally satisfactory, particularly in respect to exit site infections. Although the probability of catheter survival at 3 years (if all complications except of exit/tunnel infections were censored) increased from 0.655 to 0.790, the results indicate that 21 percent of implanted catheters cannot survive 3 years because of exit/tunnel infection (Twardowski Z.J., Prowant B.F., Khanna R., Nichols W.K., Nolph K.D.: Long term experience with Swan Neck Missouri catheters, ASAIO Transactions 1990; 36:M491-M494.). Many exit infections, although not leading to catheter removal, cause patient suffering, require prolonged antibiotic therapy, and increase the cost of treatment.

One of the important reasons for exit site infection is trauma caused by catheter pulling or tugging, pressure on the exit by a tight garment, and the movement of the patient's abdominal wall transmitting mechanical stress to the exit (Twardowski Z.J., Prowant B.F.: Can new catheter design eliminate exit site and tunnel infections? Perspectives in Peritoneal Dialysis. 1986; 4(No. 2): 5-9.). To prevent exit site infection, good catheter protection from mechanical stress is extremely important, especially during break-in; however, all efforts to immobilize the catheter with use of various devices have been only partially successful because the abdominal wall is in constant motion. This motion is transmitted to the catheter, causing a piston like movement within the sinus tract, which traumatizes the skin exit and sinus tract, and brings about bacterial penetration deep into the sinus tract. Damage to the epidermis and/or granulation tissue within the sinus tract combined with the deep bacterial penetration results in infection.

Our extensive clinical and research experience with catheter exit sites indicates that downwardly directed exits of cuffed hemodialysis catheters implanted into jugular and/or subclavian veins are less prone to infection than those of peritoneal catheters (Twardowski Z.J., Prowant B.F., Nolph K.D., Khanna R., Schmidt L.M.: Culture results of peritoneal catheter peri-exit smears (S) and sinus tract washouts (W). XIth International Congress of Nephrology, Abstracts, Tokyo, Japan, July 15-20, 1990, p. 259 A; Twardowski Z.J., Prowant B.F., Nolph K.D.,. Khanna R., Nichols W.K., C.W. Caldwell C.W., H. Taylor H., H.L. Moore H.L.: Key factors in exit site(s) (ES) evaluation. XIth International Congress of Nephrology, Abstracts, Tokyo, Japan, July 15-20, 1990, p. 26 A.). A salient difference between exits of such hemodialysis catheters and those of peritoneal catheters is their location: the chest versus the abdomen. The chest is a very sturdy structure, with minimal wall motions compared with the abdominal wall. The catheter exit located on the chest wall is thus subjected to movement only minimally, therefore is less likely to become infected. Moreover, a tight garment is usually not worn on the chest and there is less pressure on the exit.

There is controversy as to whether the external cuff is beneficial or detrimental for catheter survival. Several authors showed exit site infections to be similar with and without external cuff. Other authors noted that infection became resistant to antibiotic treatment once the tissue grown into the external cuff was infected. They considered the outer cuff to be a detriment rather than an asset for the peritoneal catheter. On the contrary, we found a beneficial effect of the outer cuff, provided that the cuff was located 1-2 cm from the exit and cuff extrusion was prevented (Twardowski Z.J., Nolph K.D., Khanna R., Prowant B.F., Ryan L.P.: The need for a "Swan Neck" permanently bent, arcuate peritoneal dialysis catheter. Perit Dial Bull 1985; 5: 219-223). Our extensive study of the morphology of the catheter tunnel suggests that the tissue ingrown into the cuff does not constitute per se a critical barrier for spreading infection (Twardowski Z.J., Dobbie J.W., Moore H.L., Nichols W.K., DeSpain J.D., Anderson P.C., Khanna R., Nolph K.D., Loy T.S.: Morphology of peritoneal dialysis catheter tunnels. Accepted for publication to Perit. Dial. Int). This observation suggests that the value of the external cuff depends on anchoring the catheter resulting in the restriction of the piston-like movement. Consequently, another anchoring structure, not a porous cuff, may better prevent exit site infection.

In accordance with this invention, the above disadvantages are reduced by the use of a modified catheter.

DESCRIPTION OF THE INVENTION

According to the present invention, a peritoneal dialysis catheter has been developed which comprises two flexible tubes which are typically connected at the time of implantation. The peritoneal dialysis catheter of this invention comprises a distal tubular section as one of the flexible tubes, and a proximal tubular section as the other. Nonintegral, tubular connector means are provided, being positioned to connect with respective ends of the proximal and distal tubular sections in sealed flow relation.

Thus, the distal tubular section may be surgically implanted into the peritoneal cavity, while the proximal tubular section may be surgically implanted into the chest of a patient with an end thereof protruding from the chest. The respective ends of the two sections may be connected to each other through the tubular connector means as the tubular sections are implanted or after such surgical implantation.

The catheter may be made of silicone rubber, polyurethane or other flexible material. The implanted distal section typically constitutes the intraperitoneal catheter segment and part of the intramural segment. The distal end of the distal section, located in the peritoneal cavity, is preferably coiled and provided with a central bore and multiple, small side perforations for fluid delivery into and drainage from the peritoneal cavity. The proximal end of the distal section preferably carries a porous cuff, preferentially located in the rectus muscle, to facilitate permanent ingrowth of the tissue into it and anhoring of the catheter into the abdominal wall.

The tubing of preferably the distal section may be provided with an outwardly extending flange circumferentially surrounding the tubing just below the cuff.

As in Twardowski U.S. Pat. No. 4,687,471, the flange may be slanted at an angle of 30 degrees to 60 degrees, preferably about 45 degrees.

The proximal end of the distal section extends no more than a few centimeters from the cuff, for connection with the tubular connector means, which is typically made of titanium, hard polytetrafluoroethylene or equivalent material. The connector means is also to be coupled with the distal part of the proximal part at the time of implantation.

The proximal tubular section comprises the remaining part of the intramural segment and the external catheter segment. The distal end bore of the proximal section communicates with the proximal end bore of the distal section through the connector means. A distal part of the proximal section typically extends substantially straight to extend along the anterior chest wall as implanted.

The proximal section typically carries two spaced, porous cuffs, a superficial cuff and a middle or central cuff. The section defines, in its natural, unstressed condition, a permanently U-shaped, bent section between the cuffs. It is generally preferred for the bent section to define an arc angle of about 180 degrees. Preferably, the substantially straight portion, that is, the distal part of the proximal section, has a length of about 6-35 cm. and preferably about 15-30 cm.

In another embodiment of the invention the external, porous cuff is substituted by an anchoring wing.

The peritoneal dialysis catheter of this invention may preferably be implanted into the patient by the following steps. Steps 1 and 2 below may be performed in either order, or simultaneously:

(1) One implants the distal tubular catheter section described above substantially in the peritoneal cavity of the patient, with a proximal end of the distal section pointing toward the chest.

(2) One implants the proximal tubular catheter section discussed above substantially in the chest of the patient with the distal end of the proximal section pointing toward the proximal end of the distal section. Also, one causes the proximal end of the proximal section to protrude outwardly from the chest, typically in a position extending downwardly.

(3) One then joins the proximal end of the distal section and the distal end of the proximal section together in sealed flow relation, after the distal and proximal sections have been at least partially implanted.

A significant advantage of the implantation method of this invention lies in the fact that the implantation can be performed from a central area of the body, adjacent the final location of the connector means, the proximal end of the distal section and the distal end of the proximal section. The necessary tunnels are formed in directions leading to the peritoneal cavity and the chest. After the respective distal and proximal tubular catheter sections have been implanted, and a cuff, typically on the distal catheter section, has been implanted preferably in the rectus muscle, a distal portion of the proximal catheter section may be cut away to cut the proximal section to the optimal length. Then both catheter sections may be connected with a tubular connector which, as previously described, may be made of titanium, polytetrafluoroethylene or the like, to provide a sealed flow connection between the two catheter sections.

If desired, the connector tubing may have serrations on the outside in a conventional manner to provide a firm retention of the respective lengths of catheter tubing which are connected to it.

DESCRIPTION OF THE DRAWINGS

FIG. 1 is a plan view of the catheter of this invention in its natural, unstressed configuration as it may preferably be implanted in the patient;

FIG. 1A is an enlarged view of the connection between the proximal end of the distal part and the distal end of the proximal part of the catheter;

FIG. 1B is an enlarged side view similar to FIG. 1A but rotated 90°, showing the angled flange, bead, and epiperitoneal cuff of the distal section of the catheter;

DESCRIPTION OF SPECIFIC EMBODIMENT

Figure 2A:
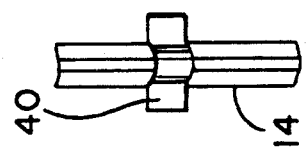
FIG. 2A is an enlarged view of another embodiment of the catheter of this invention showing the catheter having a wing instead of subcutaneous porous cuff.
Figure 2:
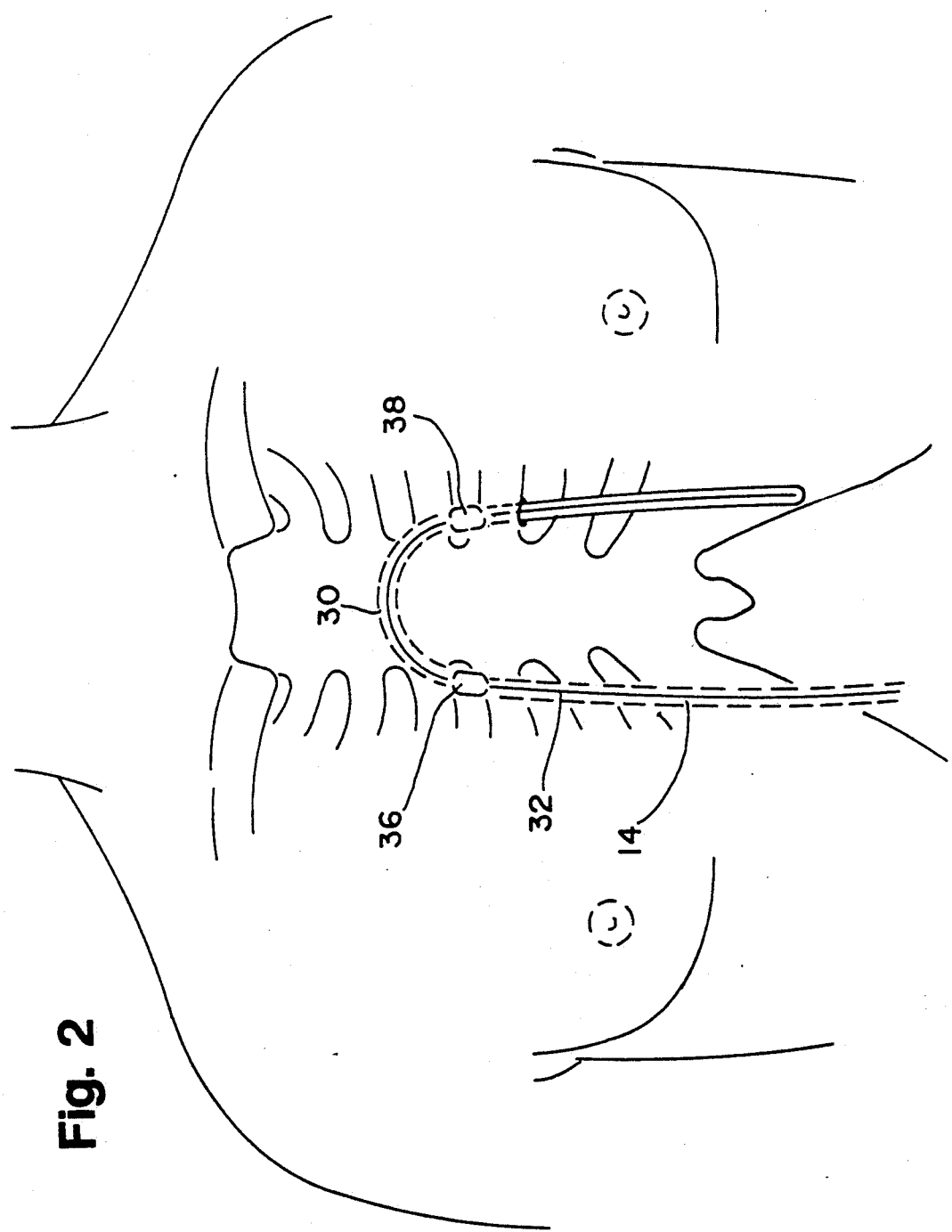
FIG. 2 is an enlarged view of the proximal part of the catheter of FIG. 1.

Referring to the drawings, peritoneal dialysis catheter 10 is shown to be of the "swan neck" type as described in the previously cited Twardowski et al patents, with specific modifications as described herein. Catheter 10 comprises a pair of flexible catheter tube sections: distal catheter section 12 and proximal catheter section 14, which may be made of a desired crosslinked elastomer such as silicone rubber, or appropriate thermoplastic materials such as polyurethane. Typically, the catheter material is relatively soft and elastomeric.

Distal catheter section 12 and proximal section 14 are shown to be implanted in the body of a patient and positioned to permit peritoneal dialysis to take place on a long term, frequent basis, with the two catheter sections being joined together by tubular connector 16, which is preferably made of titanium and which firmly fits in the bores of the tubular catheter sections 12, 14. If desired, connector tube 16 may carry a series of serrations or sharp-edged rings 17 of generally conventional design to provide strong adherence and bonding between the respective tubes and connector 16.

The distal end of distal catheter section 12 defines a spiral or coiled configuration 18 which preferably lies in a single plane when the catheter is in its natural, unstressed condition. The spiral section defines a plurality of small perforations or apertures 20 for flow communication with the exterior. Also, the distal end of catheter section 12 may itself be open for added flow communication between the peritoneal cavity and the bore of catheter 10.

Near to the proximal end 22 of distal catheter section 12 a porous cuff 24 is provided, which cuff is intended to be positioned in the rectus muscle of the belly, to serve as a tissue ingrowth retention site.

Also, angled flange 26 may be carried adjacent to and directly below cuff 24. Flange 26 is made of a plastic material which can sutured to the posterior sheath of the rectus muscle. Preferably, flange 26 is at an angle of about 45 degrees as shown.

Resilient bead 28 is then provided below flange 26. Bead 28 may be made of an elastomer such as silicone rubber, and is intended to be located in the peritoneal cavity just beneath the peritoneal membrane. A purse string suture may be applied to the groove between flange 26 and bead 28, to be tightened to prevent leakage from the peritoneal cavity along the catheter.

As shown in FIG. 1B, flange 26 and bead 28 are angled, sloping upwardly. When sutured to the posterior rectus sheath, flange 26 and bead 28 are thus angled posteriorly and upwardly relative to the abdomen. Such a position of the flange and bead helps to maintain the position of the intraperitoneal segment of the catheter in a desired downward or caudal direction.

Proximal catheter section 14 defines, in its natural, unstressed condition, a bent or U-shaped section 30 which preferably forms an arc angle of about 160–180 degrees. U-shaped section 30 is intended to be implanted in the presternal area of the chest, and is integral with two legs, 32, 34, defined by the remainder of proximal catheter section 14. It should be noted that because proximal catheter section 14 defines the U-shaped section 30 in a natural, unstressed condition, the implanted, U-shaped section does not exert significant pressure on the surrounding tissues after implantation due to any elastic memory of the catheter urging the catheter to straighten out, contrary to many catheters of the prior art. Thus, the neighboring tissue is subjected to less stress with the catheter of this invention.

The distal leg 32 forms a generally straight segment that extends to connector tube 16, preferably having a length from the distal end of curved portion 30 to the distal end of segment 14 of about 20 cm. There, it joins with connector 16 and distal catheter section 12 to provide a sealed flow path between the two catheter sections. Thus, catheter 10 comprises two catheter sections and a tubular connector which is not integral with the respective catheter sections, although providing a firm connection and seal.

After implantation, proximal leg 34 of catheter segment 14 forms the intramural segment along with the curved segment 30, and also defines the external segment of catheter 10.

A pair of porous cuffs 36, 38 are also provided at or adjacent both ends of curved, U-shaped section 30. Considering cuff 24 as being the inner cuff, the middle cuff 36 is intended to be positioned within the tissue typically of the second, third, or fourth intercoastal space on either side of the sternum. Cuff 38 serves as the superficial cuff, and is intended to be positioned within the coastal space on the opposite side of the sternum from the central cuff, and positioned about 1 or 2 centimeters from the skin exit.

As previously stated, the two catheter sections 12, 14, may be separately emplaced in the patient, following which a distal portion of proximal catheter section may be cut away to cut the section to the precisely desired length that turns out to be optimum for the particular size of the patient, and also depending on how the implantation of the two catheter sections has gone. Then, the two catheter sections may be connected together, being of the precisely desired length, by connector 16.

FIG. 2A shows an alternate embodiment of the invention where a wing 40 or other structure made of nonporous material is used as a substitute for outer cuff 38. The purpose of this structure is to anchor the proximal end of the catheter, preventing piston-like movements, but avoiding tissue ingrowth into the porous structure. As mentioned above, many authors maintain that infection of such a tissue is resistant to cure without surgical "shaving off" of the cuff with the tissue.

CATHETER IMPLANTATION TECHNIQUE

A preferred surgical technique of catheter implantation used for "swan neck" catheters is generally followed, with modifications related to the new design.

The intraperitoneal segment 18, epiperitoneal cuff 24, flange 26, and bead 28 are implanted in a manner identical to that of swan neck Missouri 2 or swan neck Missouri 3 catheters (Twardowski Z.J., Khanna R., Nichols W.K., Nolph K.D.: Swan Neck peritoneal dialysis catheters—design, insertion, break-in, and chronic care. Video, Second Edition. Academic Support Center. The Curators of the University of Missouri, 1988). As one exception, the position of the inner cuff is intended to be preferentially above the umbilicus. In brief, a 3-4 cm transverse incision is made through the skin and the subcutaneous tissue over the rectus muscle above the umbilicus. Then an incision is made in the anterior rectus sheath, and the rectus muscle fibers are dissected bluntly in the direction of the fibers down to the posterior rectus sheath. A purse string suture is placed through the posterior rectus sheath, transversalis fascia, and the peritoneum. A 5 mm incision reaching the peritoneal cavity is made with a scalpel. The catheter is threaded on a stiffening stylet and introduced deep into the true pelvis. The bead 28 is introduced into the peritoneal cavity, and the flange 26 is placed flat on the posterior rectus sheath. The stylet is removed, and then a 50 ml syringe containing sterile saline is attached to the catheter. Saline solution is injected into the peritoneal cavity. If the solution flows freely, the purse string suture is tightened, securing bead 28 in the peritoneal cavity and the flange 26 on the posterior rectus sheath. The flange 26 is sewn into the posterior rectus sheath with four sutures at twelve, nine, six and three o'clock. A small stab wound is made in the anterior rectus sheath above the transverse incision. The catheter is grasped with the hemostat and pulled through the wound. The transverse incision in the anterior rectus sheath is sewn.

The remainder of the implantation procedure is mostly specific for the new catheter design according to the invention. A 3-4 cm incision is made over the sternum preferentially at the level of the second, third, or fourth rib. A superior subcutaneous pocket is made by blunt dissection to accommodate the bent section of the proximal tube of the catheter. Below the incision two small pockets are made by blunt dissection to accommodate middle cuff 36 and superficial cuff 38 or wing 40. A trocar of the diameter of the tube is attached to the distal leg 32 of catheter section 14, and a tunnel is created to merge with the incision over the rectus muscle. The proximal end of the distal section 12 and the distal end of the proximal section 14 are trimmed to a desired length, and the junction is made between them through connector 16.

A 5 mm stab wound is made at the exit site on the chest. A trocar is then attached to the proximal end 42 of proximal section 14, and directed through the exit site. The bent portion 30 of the catheter section 14 is positioned carefully in the subcutaneous pocket. Care is taken to avoid catheter twisting. Finally, both skin incisions are closed with absorbable subcuticular sutures.

Accordingly, the catheter of this invention may be used as a permanent, indwelling peritoneal dialysis catheter having greatly reduced problems with infection and the like. Also, the catheter of this invention is less subject to trauma caused by catheter pulling or tugging, as well as pressure on the catheter exit site by a tight garment and movement of body portions adjacent the exit site. As can be seen, the catheter access site resides in the chest even though it is a catheter for peritoneal dialysis.

The specific procedures used for effecting peritoneal dialysis through the indwelling catheter of this invention are similar to those that are regularly used in other conventional peritoneal dialysis procedures.

The above has been offered for illustrative purposes only, and is not intended to limit the scope of the invention of this application, which is as defined in the claims below.

We claim:

1. A peritoneal dialysis catheter which comprises a distal tubular section and a proximal tubular section, and nonintegral, tubular connector means positionable in connected relation with respective ends of said proximal and distal tubular sections in sealed flow relation, at least one of said tubular sections carrying means for attachment of said catheter to living tissue adjacent said tubular connector means, whereby said distal tubular section may be surgically implanted in the peritoneal cavity and the proximal tubular section may be surgically implanted in the chest of a patient with an end thereof protruding from the chest, and said respective ends may be connected to each other through said tubular connector means as said tubular section are surgically implanted.

2. The peritoneal dialysis catheter of claim 1 in which said proximal tubular section defines in its natural, unstressed configuration, a substantially U-shaped bend plus a substantially straight portion distal to said bend, said substantially straight portion having a length of 6 to 35 cm.

3. The peritoneal dialysis catheter of claim 2 in which said length is 15 to 30 cm.

4. The peritoneal dialysis catheter of claim 1 in which said distal tubular section defines a perforated distal end.

5. The peritoneal dialysis catheter of claim 1 in which said distal tubular section defines a coiled distal end.

6. The peritoneal dialysis catheter of claim 1 in which said proximal tubular section carries a pair of porous cuffs spaced from the ends of said proximal section.

7. The peritoneal dialysis catheter of claim 1 in which said attachment means comprises a flange occupying an angle of 30 to 60 degrees to the axis of said catheter, and an adjacent, resilient bead surrounding said catheter to define a suture groove between said flange and bead.

8. The peritoneal dialysis catheter which comprises a distal tubular section and a proximal tubular section, and nonintegral, tubular connector means positionable in connected relation with respective ends of said proximal and distal tubular sections in sealed flow relation, said proximal tubular section defining, in its natural, unstressed configuration, a substantially U-shaped bend plus a substantially straight portion distal to said bend, said substantially straight portion having a length of 6 to 35 cm. and in which at least one of said tubular sections carries means for attachment of said catheter to living tissue adjacent said tubular connector means.

9. The peritoneal dialysis catheter of claim 8 in which said proximal tubular section carries a pair of porous cuffs, each of said porous cuffs being positioned adjacent to an end of said substantially U-shaped bend.

10. The peritoneal dialysis catheter of claim 9 in which the length of said substantially straight portion distal to said bend is 15-30 cm.

11. The peritoneal dialysis catheter of claim 9 in which said distal tubular section defines a perforated distal end, said distal end being coiled.

12. The peritoneal dialysis catheter of claim 9, said catheter having an axis along its length and in which said attachment means comprises a flange, occupying an angle of 30 degrees to 60 degrees to the axis of said catheter, and an adjacent, resilient bead surrounding said catheter to define a suture groove between said flange and bead.

* * * * *